(12) United States Patent
Moretti et al.

(10) Patent No.: US 6,225,501 B1
(45) Date of Patent: May 1, 2001

(54) OPTICALLY ACTIVE 2-AMINOTETRALINE, PROCESS FOR ITS PREPARATION AND PHARMACEUTICAL COMPOSITIONS CONTAINING SAME, ACTIVE IN PREVENTING AND TREATING SEPTIC SHOCK

(75) Inventors: Gian Piero Moretti, Rome; Piero Foresta, Pomezia, both of (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/341,762

(22) PCT Filed: Jan. 28, 1998

(86) PCT No.: PCT/IT98/00011

§ 371 Date: Jul. 16, 1999

§ 102(e) Date: Jul. 16, 1999

(87) PCT Pub. No.: WO98/33762

PCT Pub. Date: Aug. 6, 1998

(30) Foreign Application Priority Data

Feb. 3, 1997 (IT) .............................................. RM97A0050

(51) Int. Cl.$^7$ ......................... C07C 209/00; A01N 33/02
(52) U.S. Cl. ........................... 564/413; 564/428; 514/657
(58) Field of Search ..................... 564/413, 428; 514/657

(56) References Cited

U.S. PATENT DOCUMENTS 5,591,777 * 1/1997 Foresta .

* cited by examiner

*Primary Examiner*—Paul J. Killos
(74) *Attorney, Agent, or Firm*—Nixon & Vanderhye

(57) ABSTRACT

S(−)-amino-6-fluoro-7-methoxytetraline, a process for its preparation and pharmaceutical compositions containing same, active in preventing and treating septic shock, are disclosed.

8 Claims, 4 Drawing Sheets

Figure 1:
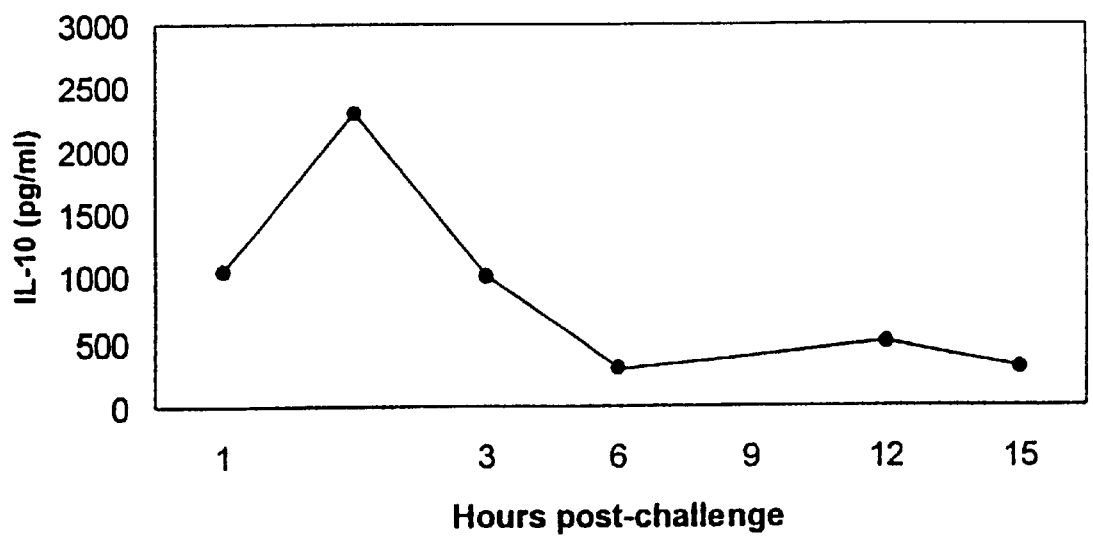

OPTICALLY ACTIVE 2-AMINOTETRALINE, PROCESS FOR ITS PREPARATION AND PHARMACEUTICAL COMPOSITIONS CONTAINING SAME, ACTIVE IN PREVENTING AND TREATING SEPTIC SHOCK

The present invention relates to S(−)-2-amino-6-fluoro-7-methoxytetraline, a process for its preparation and pharmaceutical compositions comprising same as active ingredient.

S(−)-2-amino-6-fluoro-7-methoxytetraline, both as free base and pharmacologically acceptable salt thereof, is endowed with potent therapeutical activity for treating septic shock.

Septic shock is a clinical syndrome that may set in as a result of severe infections caused by both gram-negative and gram-positive bacteria, by protozoa, or by viruses and is characterized by leukocytosis, fever, tachycardia, hypotension and renal, respiratory, cardiac and hepatic insufficiency. It should be stressed, however, that the severity of septic shock is independent of the type of micro-organism responsible for the syndrome (Parillo J. E., Pathogenetic mechanisms of septic shock, *New Engl. J. Med.*, 328:1471–1477, 1993) and is related rather to the extent of the individual inflammatory response to the agent responsible for the toxic insult.

Although there has been a significant improvement in antibiotic therapy and treatment protocols in intensive care units over the past few years, septic shock continues to be one of the major causes of morbidity and mortality in hospitalised patients. It is estimated, in fact, that in the United States it is responsible for more than 100,000 deaths per year (Glauser M. P., Zanetti G., Baumgartner J. D. and Cohen J., Septic shock: pathogenesis. *Lancet* 338:732–736, 1991).

The decisive and most influential factor in septic shock is the body's reaction to products deriving from lysis or from microbial metabolism.

Among such substances, the first to be identified and the one most extensively used in experimental research is lipopolysaccharide (LPS), which is present in the walls of gram-negative bacteria and consists chemically of a polysaccharide portion which varies according to bacterial species and a constant lipid portion (lipid A), detectable in micellar form in the blood of septicaemic subjects. If administered to experimental animals, LPS is capable of reproducing all the cardiocirculatory and neurological symptoms encountered in shock (Olson N. C., Salzer W. L., McCall C. E., Biochemical, physiological and clinical aspects of endotoxiemia. *Molec. Aspects Med.*, 10:511–629, 1988). It may therefore be regarded as the "prime mover" in the chain of events which, via activation of the intrinsic and extrinsic pathways of the coagulative cascade and the secretion of cytokines such as TNF, IL-1 and g-INF (Bone R. C., A critical evaluation of new agents for the treatment of sepsis. *J. Am. Med. Ass.*, 266:1686–1691, 1991), leads to the triggering of the clinical symptoms.

The increasing importance of this syndrome, its severity and the inadequate therapeutic means currently available make the rapid discovery of therapeutic agents capable of effectively combating the progression of the disease a highly desirable goal.

The methodological approach most widely employed for the purposes of assessing the possible protective effect of a substance in septic shock in preclinical investigations is the use of experimental models involving intoxication by a toxic substance (an endo- or exotoxin) injected directly into the laboratory animal or released in massive amounts by the infecting cells with which the animal is inoculated.

2-aminotetralines active for treating septic shock are already known. EP-A-0 730 861, which is incorporated herein by reference, filed in the name of the same applicants as those of the present application, discloses a class of such 6,7-substituted-2-aminotetralines and particularly the racemic compound (R,S)-2-amino-6-fluoro-7-methoxytetraline (ST 626).

It has now been found that the enatiomer S(−)-2-amino-6-fluoro-7-methoxytetraline exhibits a far more potent activity than the racemate (R,S)-2-amino-6-fluoro-7-methoxytetraline (ST 626) for treating septic shock.

S(−)-2-amino-6-fluoro-7-methoxytetraline can occur both as free base having the formula:

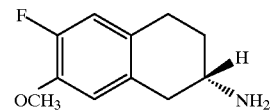

and as a salt having the formula:

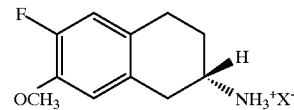

wherein $X^-$ is the monovalent anion of a pharmacologically acceptable acid.

What is meant by pharmacologically acceptable salts of S(−)-2-amino-6-fluoro-7-methoxytetraline are any of its salts with an acid that does not give rise to unwanted side effects. Such acids are well known to pharmacologists and to experts in pharmacy and pharmaceutical technology.

Non-limiting examples of such salts are chloride, bromide, orotate, acid aspartate, acid citrate, acid phosphate, fumarate and acid fumarate, lactate, maleate and acid maleate, acid oxalate, acid sulphate, glucose sulphate, tartrate and acid tatrate.

A process for preparing S(−)-2-amino-6-fluoro-7-methoxytetraline as free base or as a pharmacologically acceptable salt is illustrated in the following reaction scheme:

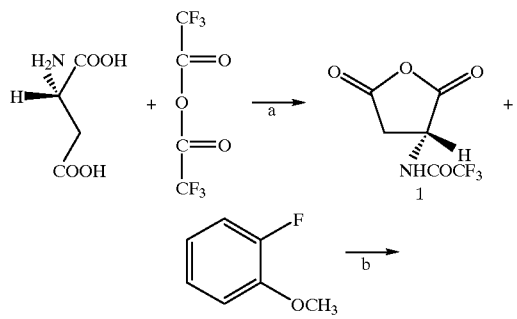

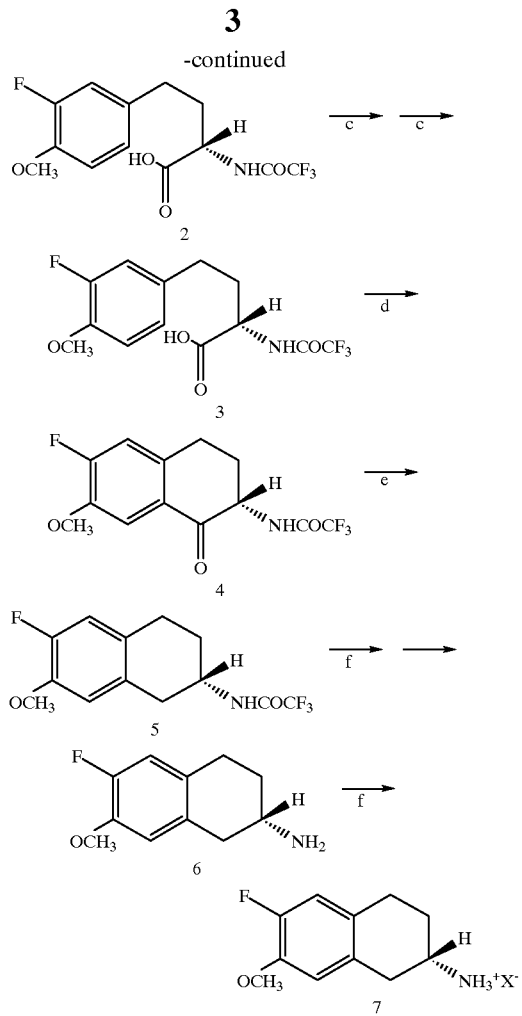

wherein X⁻ is the monovalent anion of a pharmacologically acceptable salt. The process comprises the following steps:

(a) preparing an anhydride 1 by suspending L(+)-aspartic acid in CF₃COOH, adding cold trifluoroacetic anhydride (e.g. at −20° C.) and then heating the resulting mixture to the reflux temperature until the reaction is completed; then bringing it to dryness and repeatedly washing the residue under stirring with an organic solvent which does not dissolve it;

(b) condensing the anhydride 1 with an excess of 2-fluoroanisole (1.5–3 moles) in the presence of AlCl₃ vigorously stirring with heating (40–60° C.), for 40–50 hours, thus obtaining the acid 2. In order to facilitate the stirring, a solvent (e.g. CH₂Cl₂) can be added. The solid thus obtained is filtered off, treated with cooling (0° C.–8° C.) with conc. HCl (e.g. 6M), the acid aqueous phase is extracted with a solvent (e.g. ethyl ether), the organic phase is brought to dryness and the compound 2 is purified by crystallization;

(c) reducing the acid 2 by dissolving it with CF₃COOH, cooling the solution thus obtained to 0–8° C., adding an excess amount of triethylsilane (e.g. 6M) and cautiously heating the mixture to the reflux temperature until the reaction is completed (about 4 hours). The reaction mixture is brought to dryness, the oily residue is dissolved with an alkaline aqueous solution (pH 10), the undissolved residue is filtered off, the filtrate is acidified (pH 3) and the product is extracted with a precipitating solvent (e.g. CH₂Cl₂); the product is brought to dryness and purified by crystallization, thus obtaining the compound 3;

(d) preparing the tretralone 4 from the compound 3 by condensation via Friedel-Crafs reaction, with PCl₅ and AlCl₃ in an inert anhydrous organic solvent;

(e) reducing the tetralone 4 by suspending it in boroetherate trifluoride and adding an excess amount of triethylsilane (molar ratio: 3–6) at 0–8° C. and letting the reaction to proceed at room temperature until the reaction is completed (60–90 hours); adding an aqueous alkaline solution (pH 9), extracting the aqueous phase with a solvent, bringing to dryness and purifying by crystallization, thus obtaining the compound 5;

(f) hydrolyzing the compound 5 with an aqueous alkaline solution, extracting wih a solvent (e.g. ethyl ether), bringing to dryness and purifying by crystallization the S(−)-2-amino-6-fluoro-7-methoxytetraline 6 thus obtained;

(g) in order to optionally obtain the salified tetraline (e.g. as hydrochloride) solubilizing the compound 6 in an organic solvent (e.g. CH₃OH, ethyl ether), acidifying with the desired H⁺X⁻ acid and bringing to dryness and optionally purifying the compound by crystallization.

With reference to the foregoing reaction scheme, the preparation of the compound of the present invention (as hydrochloride) is described hereinbelow.

EXAMPLE

Preparation of S(−)-2-amino-6-fluoro-7-methoxytetraline hydrochloride (ST 1214)

a) Preparation of S(−) trifluoro acetylaspartic anhydride 1.

L(+)-aspartic acid (100 g; 0.75 moles) was suspended in trifluoroacetic acid (300 mL); the resulting suspension was kept under stirring and cooled to −20° C. with an ice/salt bath. Trifluoroacetic anhydride (300 mL; 2.16 moles) was slowly added thereto under stirring. The mixture was then cautiously refluxed at 45° C. overnight.

When the reaction ended, the mixture was completely brought to dryness in an evaporator and the solid residue was washed three times under stirring with hexane, each time removing the hexane by decantation; the residue was again completely brought to dryness. Finally, the residue was triturated under stirring with hexane-ethyl ether, the resulting mixture was filtered and the residue was dried under vacuum. 150 g of the compound 1 were obtained (yield 95%).

M.P.=140–142° C.

$[\alpha]_D$=−40.7° (c=1% MetOH); analysis: corresponding.

b) Preparation of S(+)-4-(3-fluoro-4-methoxyphenyl)-4-oxo-2(N-trifluoroacetyl)aminobutanoic Acid 2.

S(−)-trifluoroacetylaspartic anhydride (150 g; 0.712 moles) was suspended in 2-fluoroanisole (300 mL; 2.67 moles), the resulting mixture was vigorously stirred and then anhydrous aluminium chloride (240 g; 1.57 moles) was slowly added thereto portionwise. When the addition was completed, the mixture was kept under vigorous stirring at 40–45° C. for 24 hours. Anhydrous CH₂Cl₂ and further 60 g of AlCl₃ were added and the reaction mixture was kept under stirring for further 48 hours.

The solid residue was then treated wih one liter of CH₂Cl₂ by grinding it under stirring. The methylene chloride containing the excess of fluoroanisole was separated. The solid residue was filtered off and added portionwise to 2 liters of 6M HCl kept under vigorous stirring. At the end of addition, the mixture was kept under stirring for 30 minutes. The acid phase was then repeatedly extracted with ethyl ether. The ether phases were pooled, washed with water, dried over anhydrous $Na_2SO_4$ and then brought to dryness. A raw solid residue was obtained which was crystallized from 1:1 AcOEt/hexane. 188 g of compound 2 were obtained (yield 78.3%):

M.P.=113–115° C.

$[\alpha]_D$=+27.5° (c=1% MetOH); analysis: corresponding.

c) Preparation of S(+)-4-(3-fluoro-4-methoxyphenyl)-2-(N-trifluoroacetyl)aminobutanoic acid 3.

Compound 2 (100 g; 0.297 moles) was dissolved in trifluoroacetic acid (500 mL). The resulting solution was cooled to 0° C. and triethylsilane (300 mL; 1.89 moles) was slowly added thereto. When the addition was completed, the mixture was slowly brought to its boiling point and kept at the boiling temperature for 4 hours. The mixture was then completely brought to dryness in an evaporator, the residue was twice washed with ethyl ether, each time bringing the mixture to dryness to wholly remove the trifluoroacetic acid. The oily residue thus obtained was cooled to −20° C. with an ice/salt bath and then treated under stirring with a $NaHCO_3$ saturated solution whose pH had been adjusted to 10 with 4NNaOH. The final alkaline phase was cautiously acidified to pH 3 with 6N HCl, at 0° C. A precipitate was obtained which was repeatedly extracted with $CH_2Cl_2$. The organic extracts were pooled, washed with a little amount of water, dried over anhydrous $Na_2SO_4$ and brought to dryness. The oily residue was dissolved in a little amount of ethyl acetate and precipitated with hexane under stirring. The mixture was kept under stirring overnight, filtered and the residue was dried. 72 g of the compound 3 were obtained (yield 75%).

M.P.=113–115° C.

$[\alpha]_D$=+11.3° (c=1% MetOH); analysis: corresponding.

d) Preparation of S(−) (N-trifluoroacetyl)amino-6-fluoro-7-methoxy-1-tetralone 4.

Compound 3 (70 g; 0.217 moles) was dissolved in an anhydrous methylene chloride (1400 mL). The resulting mixture was cooled to 0° C. with an ice bath and then $PCl_5$ (70 g; 0.336 moles) was slowly added thereto. At the end of the addition, the mixture was kept under stirring at 0° C. for about 2 hours, then cooled to −20° C. $AlCl_3$ (56 g; 0.42 moles) was added portionwise to the mixture. Following the addition, the mixture was kept for about 2 hours at room temperature and then cautiously heated at the boiling point and kept at the boiling temperature for about 6 hours. The mixture was then cooled to 0° C. and crushed ice (about 300 mL) was added portionwise thereto to destroy the excess of reactants. The mixture was extracted three times with $CH_2Cl_2$. The organic phases were pooled, dried over anhydrous $Na_2SO_4$ and brought to dryness; a yellowish solid was obtained which was dissolved in a little volume of ethyl acetate and then precipitated with hexane. 40 grams of compound 1 were obtained (yield: 60.4%).

M.P.=184–185° C.

$[\alpha]_D$=−55.4° (c=1% MetOH); analysis: corresponding.

e) Preparation of S(−)-2-(N-trifluoroacetyl)amino-6-fluoro-7-methoxytetraline 5.

Compound 4 (40 g; 0.131 moles) was suspended in boroetherate trifluoride (340 mL) at 0° C. Triethylsilane (90 mL; 0.567 moles) was added to the suspension at 0° C. and the resulting mixture was kept for about 4 days at room temperature. At the end of the reaction, a $NaHCO_3$ saturated solution (pH 8–9) was added to the reaction mixture and the aqueous phase was extracted four times with $CH_2Cl_2$. The pooled organic phases were washed with water, dried over anhydrous $Na_2SO_4$ and brought to dryness. The raw compound thus obtained was recrystallized from isopropyl ether. 30 g of compound 5 were obtained (yield: 78.63%).

M.P.=45–47° C.

$[\alpha]_D$=−80° (c=1% MetOH); NMR: corresponding.

f) Preparation of S(−)-2-amino-6-fluoro-7-methoxy tetraline hydrochloride (ST 1214)

Compound 5 (30 g; 0.103 moles) was dissolved in methanol (225 mL) and water (225 mL) containing $K_2CO_3$ (54 g; 0.391 moles). The resulting solution was refluxed under stirring for 3 hours. Methanol was removed under vacuum and further 100 mL of water were added to the solution. The organic phases were pooled, dried over anhydrous $Na_2SO_4$, filtered and brought to dryness. The oily residue thus obtained was dissolved in ethyl ether, acidified with HCl (15% solution in ethanol) and the precipitate was filtered off and redissolved in methanol, decolored with activated charcoal, filtered, concentrated under vacuum and finally crystallized from n-propanol.

Crystallization was twice repeated, giving 12.6 g of compound 7.

($X^-$=Cl) (yield 52.80%)

M.P.=263–265° C.

$[\alpha]_D$=−52.5° (c=1% $H_2O$)

$NMRD_2O\delta70$-6.8 (m, 2H, aromatic); 3.8 (s, 3H, $OCH_3$);

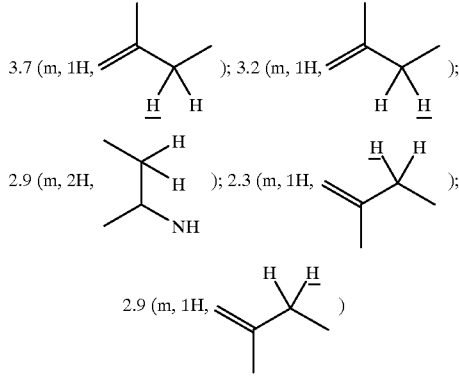

The present invention also relates to the use of S(−)-2-amino-6-fluoro-7-methoxytetraline both as free base and pharmacologically acceptable salt thereof for preparing a medicament effective for the therapeutical treatment of septic shock.

This medicament can occur as an orally or parenterally administrable pharmaceutical composition, wherein the active ingredient is S(−)-2-amino- 6-fluoro-7-methoxytetraline free base or a pharmacologically acceptable salt thereof in admixture with suitable pharmacologically acceptable excipients, whose selection shall be apparent to any expert in pharmacy and pharmaceutical technology. Whilst the oral administration form is suitable for preventing septic shock, the parenterally administrable composition, particularly via the intravenous route, is the composition of choice for administration thereof to patients in septic shock.

The following pharmacological tests show the results obtained with the compound of this invention, S(−)-2-amino-6-fluoro-7-methoxytetraline hydrochloride (ST 1214) in comparison with the reference compound (R,S)-2-amino-6-fluoro-7-methoxytetraline hydrochloride (ST 626) in experimental models of septic shock.

These comparison tests show a far higher preventive and therapeutical activity of the compound of the invention ST 1214 in comparison with the known compound ST 626 and also provide elucidations on possible action mechanisms responsible for the favourable pharmacological profile of the compound: dramatic lowering of haematic and tissue TNF levels and of serum NO release which accompany a remarkable increase of the levels of the antiinflammatory IL-10 cytokine.

EVALUATION OF THE EFFECT OF ST 626 AND ST 1214 ON THE LETHALITY INDUCED BY LIPOPOLYSACCHARIDE (LPS FROM E. coli O26:B6 OR FROM S. typhosa) IN BALB/c MICE Animals BALB/c inbred male mice (Iffa Credo), aged approx. 7 weeks, were utilized (20–40 animals per experimental group).

Experimental Procedure

Compounds ST 626 and ST 1214, solubilized in sterile saline, were intravenously (i.v.) administered at the dose of 6 mg/kg (approx. equal to 1/10 LD50) 30 min prior to and again 5 min after endotoxic challenge (LPS). Prior to use, LPS (either from *E. coli* serotype O26:B6 or from *S. typhosa*) was first solubilized in sterile saline and then injected intraperitoneally (i.p.) at the dose of 10 mg/kg (*E. coli* LPS) and 23 mg/kg (*S. typhosa* LPS) in a volume of 0.1 ml per 10 gr of animal body weight (b.w.). Survival was assessed daily for 10 days following LPS challenge, taking note of the day when each of the animals died.

RESULTS

The results obtained with ST 626 and ST 1214 in these two models of endotoxic shock are reported in Table 1 and Table 2.

Compound ST 626 appears, to some extent, to reduce the lethality induced either by *E. coli* or *S. typhosa* LPS, being able to increase survival up to 14% and 40%, in the respective models. ST 1214 efficacy results to be greater than ST 626 as in the shock induced by LPS from *E. coli* and by LPS from *S. typhosa* survival increased up to 37% (p<0.002) and up to 65% (p<0.001), respectively.

TABLE 1

Effect of ST 626 and ST 1214 i.v. administrations on the lethality induced in mice[a] by injection of *E. coli* LPS (serotype O26:B6).

| Experimental group | Treatment[b] | Lethality D/T[c] | Survival increase[d] (%) | P[e] |
|---|---|---|---|---|
| LPS (10 mg/kg) | — | 31/39 | — | |
| ST 626 (6 mg/kg) | −30' and +5' | 25/38 | 14 | n.s. |
| LPS (10 mg/kg) | — | 28/30 | — | |
| ST 1214 (6 mg/kg) | −30' and +5' | 17/30 | 37 | <0.002 |

[a]BALB/c mice
[b]Time of compound administration with respect to the LPS challenge
[c]Dead/Total in each experimental group
[d]Survival increase (%) of treated animals with respect to LPS control
[e]Statistical significance was evaluated by one-tailed Fisher's exact test.

TABLE 2

Effect of ST 626 and ST 1214 i.v. administrations on the lethality induced in mice[a] by injection of *S. typhosa* LPS.

| Experimental group | Treatment[b] | Lethality D/T[c] | Survival increase[d] (%) | P[e] |
|---|---|---|---|---|
| LPS (23 mg/kg) | — | 14/20 | — | |
| ST 626 (6 mg/kg) | −30' and +5' | 6/20 | 40 | <0.05 |
| LPS (23 mg/kg) | — | 14/20 | — | |
| ST 1214 (6 mg/kg) | −30' and +5' | 1/20 | 65 | <0.001 |

[a]BALB/c mice
[b]Time of compound administration with respect to the LPS challenge
[c]Dead/Total in each experimental group
[d]Survival increase (%) of treated animals with respect to LPS control
[e]Statistical significance was evaluated by one-tailed Fisher's exact test.

EVALUATION OF THE EFFECT OF ST 626 AND ST 1214 ON THE LETHALITY INDUCED BY LIPOPOLYSACCHARIDE (LPS FROM E. coli SEROTYPE O26:B6) IN BALB/c MICE SENSITIZED WITH D-GALACTOSAMINE Animals BALB/c inbred male mice (Iffa Credo), aged approx. 7 weeks, were utilized (28–30 animals per experimental group).

Experimental Procedure

Animals were sensitized with D-galactosamine (1000 mg/kg, i.p.) and at the same time were injected with *E. coli* LPS (0.05 mg/kg, i.p.) in a total volume of 200 μl. This dose of LPS is approx. equal to DL80 in animals sensitized with D-galactosamine.

Compounds ST 626 and ST 1214 were i.v. administered in a volume of 200 μl of sterile saline at the dose of 6 mg/kg, approx. corresponding to 1/10 DL50, 30 min before challenge. A second i.v. administration of the compounds (at the same dose) was given 5 min following endotoxin injection.

Survival was assessed daily for 10 days following LPS challenge, taking note of the day when each of the animals died.

RESULTS

The survival increase in the animals treated with ST 1214 with respect to the one observed with ST 626 results to be frankly greater (26% vs. 11%) (Table 3).

Therefore, ST 1214 administration appears to be more effective than ST 626, in terms of animals that survived to the toxic challenge, also in this model where shock was induced with endotoxin in D-galactosamine-sensitized animals.

TABLE 3

Effect of ST 626 and ST 1214 i.v. administrations on the lethality induced by injection of LPS (from *E. coli* serotype O26:B6) in mice[a] sensitized with D-galactosamine.

| Experimental group | Treatment[b] | Lethality D/T[c] | Survival increase[d] (%) | P[e] |
|---|---|---|---|---|
| LPS (0.05 mg/kg) | — | 25/29 | — | |
| ST 626 (6 mg/kg) | −30' and +5' | 21/28 | 11 | n.s. |
| LPS (0.05 mg/kg) | — | 26/30 | — | |
| ST 1214 (6 mg/kg) | −30' and +5' | 18/30 | 26 | <0.002 |

[a]BALB/c mice
[b]Time of compound administration with respect to the LPS challenge
[c]Dead/Total in each experimental group
[d]Survival increase (%) of treated animals with respect to LPS control
[e]Statistical significance was evaluated by one-tailed Fisher's exact test.

EVALUATION OF THE EFFECT OF ST 626 AND ST 1214 ON NITRIC OXIDE SERUM LEVELS FOLLOWING INJECTION OF E. coli LPS IN BALB/c MICE

MATERIALS AND METHODS

Animals

BALB/c inbred male mice (Iffa Credo), aged 6–7 weeks, were utilized (5–9 animals per experimental group).

Treatment

Before being experimentally utilized, E. coli endotoxin (LPS serotype O26:B6) was first dissolved in sterile saline and then injected via endoperitoneal route (5 mg/kg). ST 626 and ST 1214 were i.v. administered (8 mg/kg) 5 and again 30 min following LPS challenge (time 0). Treatment with reference compound Aminoguanidine (20 mg/kg) was performed i.p. according to the same protocol as ST 626 and ST 1214.

Blood Sampling

In the experiments aimed at evaluating the effect of ST 626 and ST 1214, blood samples were taken at 20 hours after LPS challenge, when peak levels of circulating NOx (nitrates and nitrites, stable end-products of NO) were observed. Blood was withdrawn from retro-orbital sinus of ether-anesthetized animals and collected in heparinized tubes. Samples were centrifuged at 2000×g for 10 min and plasma was stored at −80° C. before NOx assay.

NOx Assay

Prior to assay, samples were diluted 1:3 with distilled water and then subjected to ultrafiltration (Millipore Ultrafree-MC 10,000 NMWL filters, Cat # UFC3LGC00) at 4700×g for 90 min. NOx concentration in the filtrates was measured by using the commercial kit available from Cabru (Nitrate/Nitrite assay Kit, Cat #780001).

Statistical Analysis

Data were analyzed by using the two-tailed Student's t test.

RESULTS

ST 1214 administration at 5 and 30 min after LPS challenge caused an evident (38%) and significant decrease ($p<0.01$) in plasma NOx levels (Table 4). The decrease of circulating NOx levels following treatment with ST 626, however, resulted to be of slighter degree (Table 4).

TABLE 4

Effect of ST 626 and ST 1214 on NOx plasma levels ($\mu$M) following E. coli LPS injection in BALB/c mice. Compounds were i.v. administered (8 mg/kg) 5 and again 30 min after LPS challenge (5 mg/kg, i.p.). Aminoguanidine (AG, reference compound) was administered via endoperitoneal route according to the same experimental protocol as ST 1214 and ST 626.

| Experimental conditions | n | NOx ($\mu$M) x ± SEM | NOx concentration decrease (%)[a] |
|---|---|---|---|
| LPS | 6 | 453.59 ± 13.29 | — |
| LPS + ST 626 | 8 | 359.38 ± 37.98 | 21 |
| LPS | 9 | 891.05 ± 51.49 | — |
| LPS + AG | 5 | 408.75 ± 50.50 | 65 |
| LPS + ST 1214 | 9 | 558.55 ± 80.81 | 38 |

[a]Percent decrease of plasma NOx levels of treated groups with respect to the relevant controls.

EVALUATION OF THE EFFECT OF ST 626 AND ST 1214 ON SERUM IL-10 (INTERLEUKIN 10) LEVELS INDUCED IN BALB/c MICE INJECTED WITH LPS FROM *Salmonella typhosa*

Animals

BALB/c inbred male mice (Iffa Credo), aged 6 weeks, were utilized (6–7 animals per experimental group).

Treatment

*Salmonella typhosa* endotoxin (LPS) was dissolved in sterile saline and then injected via endoperitoneal route at the dose of 15 mg/kg. Compounds ST 626 and ST 1214 were similarly dissolved in sterile saline and i.v. administered (8 mg/kg) 30 min prior to and again 5 min after LPS challenge.

Blood Sampling

In the experiments aimed at ascertaining the time course of IL-10 appearance in the circulation, blood samples were taken at differing times after LPS injection. In those experiments carried out to evaluate the effect of substance admininistration, blood samples were taken at 45 and 90 min after challenge. Blood was withdrawn from retro-orbital sinus of ether-anesthetized animals. Blood samples were allowed to clot at room temperature for 2 hours to separate serum, which was then centrifuged at 2000×g for 20 min. Serum samples were stored at −80° C. until assayed for IL-10 activity.

IL-10 Assay

The IL-10 serum concentrations were determined by using the ELISA kit for murine IL-10 (Genzyme, Boston, Mass.) and following the manufacturer's instructions.

Statistical Analysis

Data were analyzed by using the one-tailed Student's t test.

RESULTS

The initial experiments were carried out to determine the kinetics of IL-10 release in the circulation. The experimental data showed that detectable IL-10 levels are present as soon as 1 hour after injection of S. typhosa LPS. In our experimental conditions, IL-10 levels reach peak-values at 1.5 hr following 15 mg/kg LPS challenge (FIG. 1).

Figure 2:
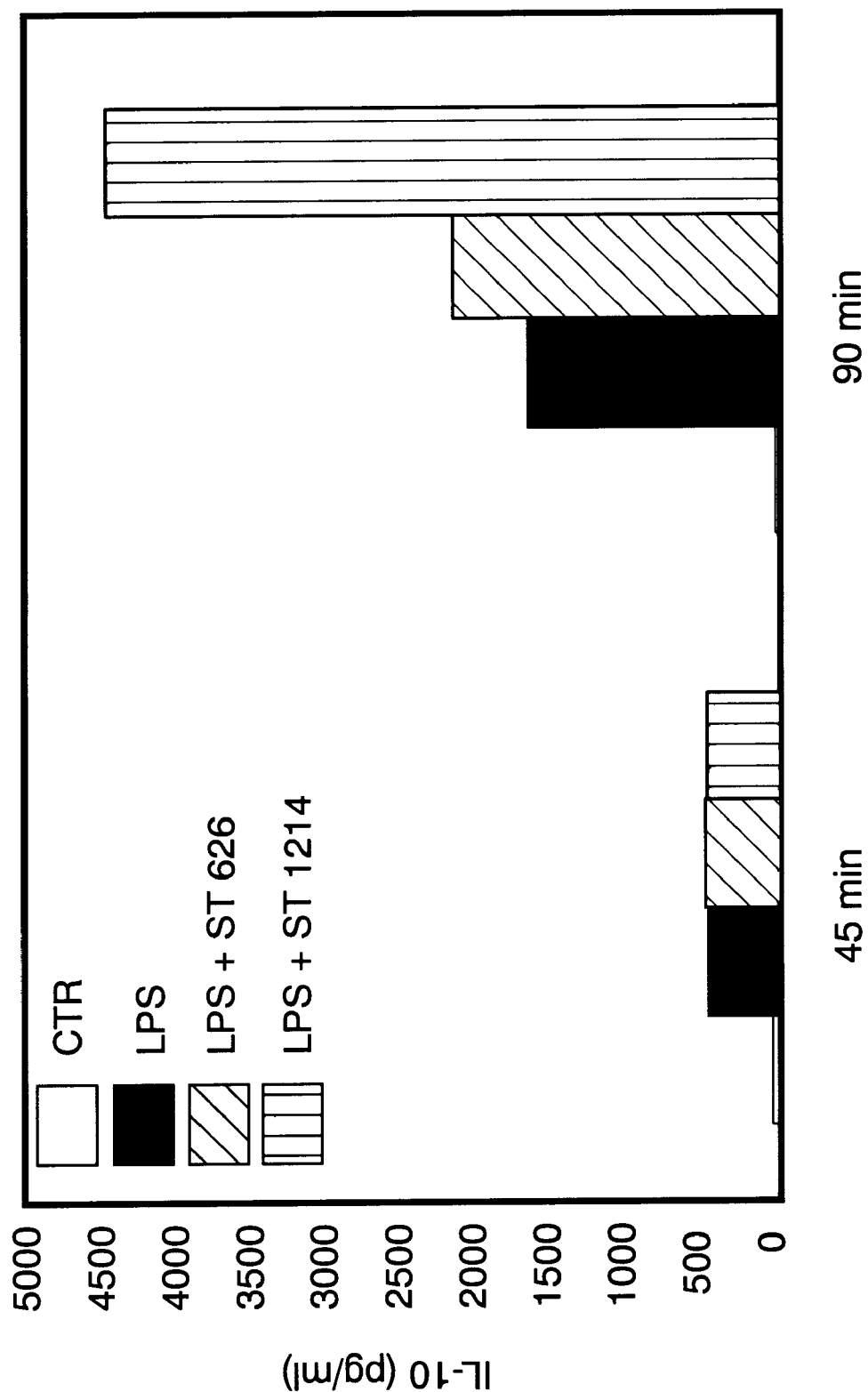

Next experiments were performed to assess whether ST 626 and ST 1214 were capable of modulating IL-10 levels following their administration at 30 min prior to and again 5 min after the toxic challenge (time 0). The data showed that ST 1214 caused approximately a 3-fold increase of IL-10 levels induced by LPS at 90 min after its injection. Conversely, ST 626 was devoid of any significant effect on IL-10 levels induced by LPS (FIG. 2). IL-10 levels at 45 min following LPS challenge were not affected, even though it has to be mentioned that the values were too close to the lower detection limit of the assay. Interestingly, ST 1214 per se was devoid of any direct modulatory effect on IL-10 serum levels. It would, therefore, seem likely that the effects observed after ST 1214 treatment are ascribable to ST 1214 ability to interfere with the normal pathways of LPS-evoked signalling.

EVALUATION OF THE EFFECT OF ST 626 AND ST 1214 ON SERUM TNF (TUMOR NECROSIS FACTOR) LEVELS INDUCED IN BALB/c MICE INJECTED WITH LPS FROM S. typhosa Animals BALB/c inbred male mice (Iffa Credo), aged approx. 5–6 weeks, were utilized (4–7 animals per experimental group).

Treatment

Endotoxin (LPS from *Salmonella typhosa*) was dissolved in sterile saline before injection via endoperitoneal route at a dose (10 mg/kg) corresponding to DL80. Similarly, compounds ST 1214 and ST 626 were dissolved in sterile saline before being administered (8 mg/kg) twice at −30 and +5 min with respect to LPS injection.

Blood sampling

Blood samples were taken at 45 and 90 min (i.e. when TNF reached peak levels) after challenge. Blood was withdrawn from retro-orbital sinus of previously ether-anesthetized animals.

Blood samples were allowed to clot at room temperature for 2 hours to separate serum, which was then centrifuged at 2000×g for 20 min. Serum samples were stored at −80° C. until assayed for cytokine (TNF) activity.

TNF Assay

TNF biological activity was determined by using the L929 tumor cell line (a murine fibrosarcoma), which is very sensitive to the TNF cytotoxic activity (V. Ruggiero, C. Chiapparino, S. Manganello, L. Pacello, P. Foresta & E. Arrigoni Martelli. *Beneficial Effects of a Novel Platelet-Activating Factor Receptor Antagonist, ST 899, on Endotoxin-Induced Shock in Mice, SHOCK*, 2, 4:275–280, 1994). In detail, L929 cells were seeded at the density of $3.2 \times 10^5$ cells/ml in a flat-bottomed 96-well microtiter plate (100 μl/well) in RPMI-1640 culture medium containing 10% FCS. After incubation for 18 h at 37° C. and 5% $CO_2$, culture medium was discarded and serial dilutions (carried out in RPMI-1640 1% FCS) of serum samples were added. Lastly, Actinomycin-D was added to the wells (100 μl/well) at a final concentration of 1 μg/ml. This inhibitor of RNA transcription enhances L929 cell line sensitivity toward TNF cytotoxic effect. After further incubation for 18–24 hr, cells were stained with a freshly-prepared solution of 1 mg/ml XTT (sodium 3'-[1-[(phenylamino)-carbonyl]-3,4-tetrazolium]-bis(4-methoxy-6-nitro) benzene-sulfonic acid hydrate) and 125 μM PMS (phenazine methosulfate) (N. W. Roehm, G. H. Rodgers, S. M. Hatfield & A. L. Glaserbrook. *An improved colorimetric assay for cell proliferation and viability utilizing the tetrazolium salt XTT: J. Immunol. Meth.*, 142:257–265, 1991). Cells were stained by adding 50 μl/well of XTT/PMS staining solution and incubating for 2–2.5 h. After staining, the absorbance of each sample at 450 nm and at 620 nm (reference absorbance) was measured, and the resulting values were converted into TNF units, defined as the reciprocal of the dilution necessary to cause 50% cell cytotoxicity.

Statistical Analysis

Data were analyzed by using the one-tailed Student's t test.

RESULTS

Figure 3:
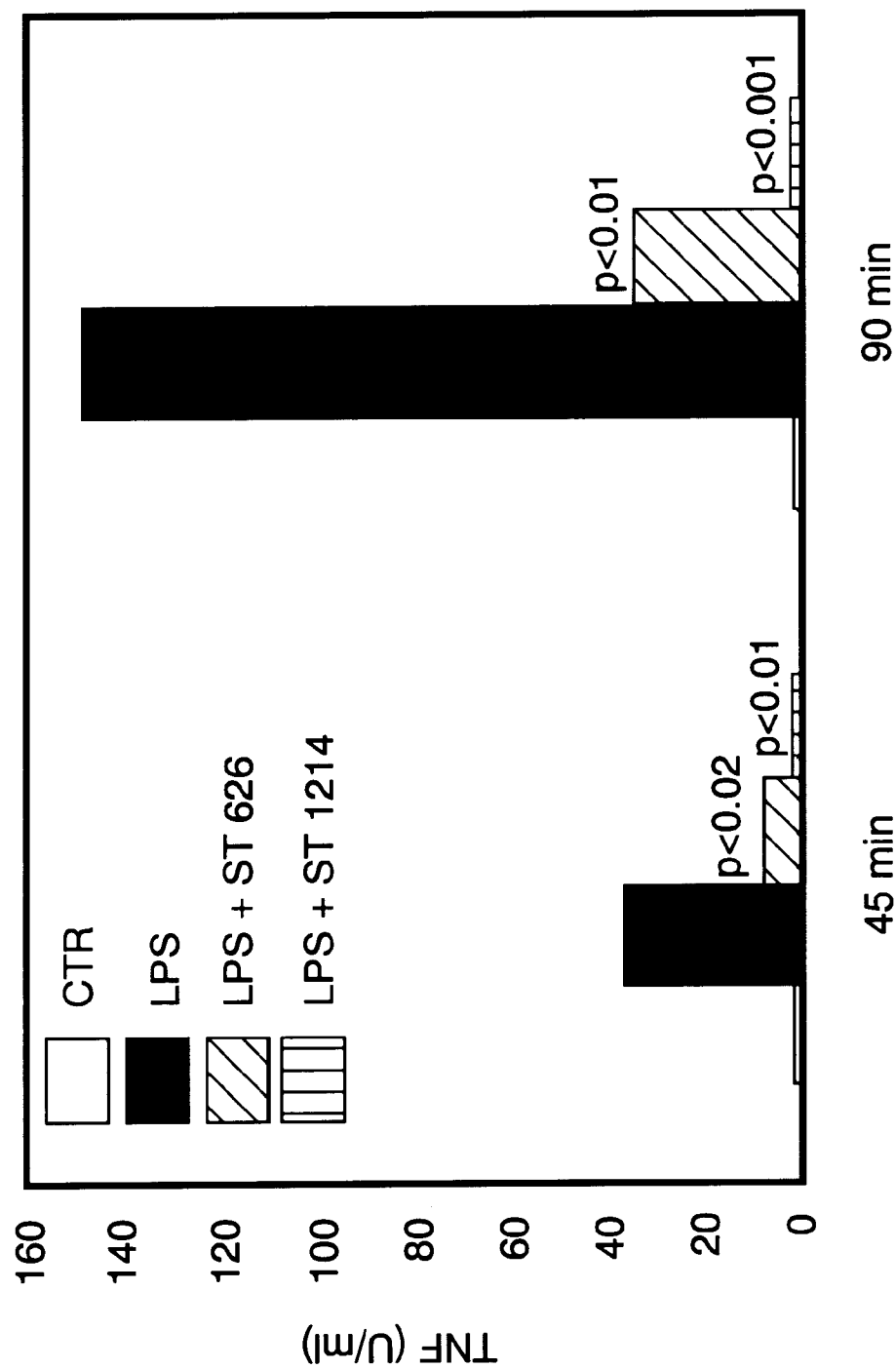

As shown in FIG. 3, ST 1214 significantly decreases circulating TNF levels both at 45 min after LPS injection ($p<0.01$) and, mostly, at 90 min (i.e. when TNF levels reached peak values) following challenge ($p<0.001$). ST 626 also down modulates serum TNF levels in mice injected with LPS, even though to a lesser degree than ST 1214 (80% vs. 99% decrease, respectively). Additionally, neither ST 1214 nor ST 626 per se have any modulatory effect on TNF levels in LPS-untreated mice.

EVALUATION OF THE EFFECT OF ST 626 AND ST 1214 ON TNF-α mRNA LEVELS IN DIFFERENT ORGANS FROM LPS-INJECTED MICE

MATERIALS AND METHODS

Animals

BALB/c inbred male mice (Iffa Credo) aged approx. 5 weeks have been utilized (4 animals per experimental group).

Treatment and Organ Excision

Treatment with ST 626 and ST 1214 was performed by double i.v. administration (8 mg/kg) at −30 and +5 min with respect to LPS challenge. Endotoxin (LPS from *S. typhosa*) was i.p. injected at the dose of 23 mg/kg, corresponding to DL80. Animals were sacrificed, via $CO_2$-asphyxiation, 45 min after LPS injection. Organs under investigation (lungs, spleen, liver and kidneys) were quickly removed, frozen in liquid nitrogen, and stored at −80° C. until RNA extraction.

RNA Extraction

RNA was isolated by a purification procedure based on centrifugation on cesium chloride gradient (J. Sambrook, E. F. Fritsch, T. Maniatis, *Molecular Cloning: A Laboratory Manual*, Second edition, Cold Spring Harbor Laboratory Press, 7.3–7.79, 1989). Briefly, organs were homogenized in 9.5 ml of a guanidine isothiocyanate solution (4 M). Lysates were layered on top of a 4-ml cesium chloride solution (5.7 M) and underwent centrifugation at 174,000×g for 24 h. RNA pellets thus obtained were dissolved in 300 μl sodium acetate (0.3 M pH 6.0) and then precipitated with 700 μl absolute ethanol at −80° C. for 24 h. Next day, RNA was centrifuged, dried and resuspended in an adequate volume of diethyl-pyrocarbonate-treated $H_2O$. In order to improve the purity of the samples, extraction was brought about with an equal volume of a 1:1 phenol/chloroform solution followed by a second extraction with an equal volume of chloroform. RNA concentration was spectrophotometrically measured and its integrity was assessed by agarose-gel electrophoresis.

Reverse Transcription-Polymerase Chain Reaction (RT-PCR).

Single-helic cDNA was synthesized by using a commercial kit from Boehringer Mannheim according to the manufacturer's instructions. Briefly, each sample of total RNA (1 μg) was added with 20 units avian myeloblastosis virus reverse transcriptase and with 1.6 μg oligo-dT primer in a final volume of 20 μl. Samples were then incubated 10 min at 25° C. to allow annealing of primers to take place. Polymerization reaction was performed for 2 h at 42° C. and then stopped by denaturing the enzyme at 100° C. for 5 minutes. Each sample was added with 80 μl $H_2O$ and kept at −20° C. until amplification. The cDNA samples thus obtained (with the procedure described above) were amplified by using a couple of specific TNF-α primers from Clontech, and following the manufacturer's instructions. Briefly, 4 μl of each sample were added with Taq polymerase (2.5 units), primers specific for TNF-α (0.4 μM) and deoxyribonucleotides (0.2 mM). Amplification reaction was performed for 30 cycles, each cycle including the following steps:

Step 1: 45 sec at 94° C. (denaturation)
Step 2: 45 sec at 60° C. (annealing)
Step 3: 2 min at 72° C. (polymerization).

After the 30 cycles were complete, samples were maintained at 72° C. for 7 min (elongation reaction).

Amplified products were separated by electrophoresis on 2.0% agarose-gel and the band intensity was analyzed by a densitometer. All samples were amplified also for a constitutive gene (β-actin), to make sure that cDNA-amplification products were really the same in the different samples.

In each reaction, controls were included as follows: a positive control; a negative control (reaction buffer alone) and, lastly, a sample whose cDNA products were obtained from a reaction lacking reverse transcriptase. The latter control allows to rule out the presence of genomic DNA in the initial RNA sample. Both cDNA synthesis and amplification reactions were performed by using the GENEAMP PCR SYSTEM 2400 thermal cycler (Perkin Elmer).

RESULTS AND CONCLUSIONS

Figure 4:
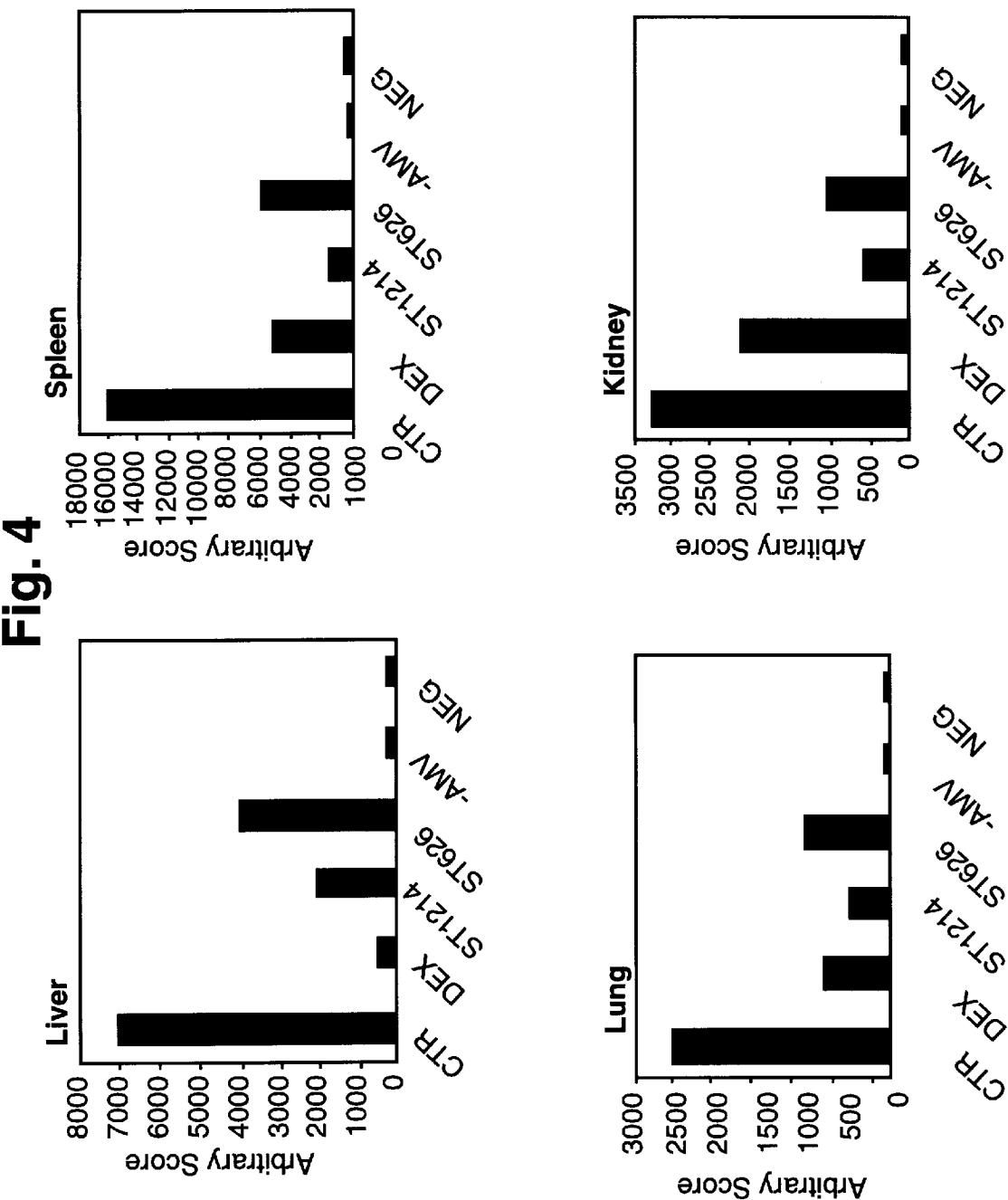

FIG. 4 shows the data obtained from a band densitometric analysis consequent to amplification of cDNA from different samples for TNF-α. As it can be seen, in all the organs (Kidneys, Spleen, Lungs, Liver) of ST 1214-treated animals a striking reduction of TNF-α mRNA levels can be observed with respect to animals injected with LPS solely. Dexamethazone, used as a positive control, causes a TNF-α mRNA decrease that appears to be higher than ST 626 only in the liver. Intensity values of bands are expressed as arbitrary units and have been normalized with respect to the expression of a constitutive gene (β-actin). In each experiment, a reaction-buffer negative control (Neg) and a control lacking reverse transcriptase (-AMV) were included. It can be concluded, therefore, that ST 1214 is able to interfere in TNF-α mRNA expression in different organs with the ensuing decrease of TNF serum levels. ST 626 is similarly able to down modulate TNF-α mRNA expression, but this decrease is lower than ST 1214.

What is claimed is:

1. S(−)-2-amino-6-fluoro-7-methoxytetraline having formula:

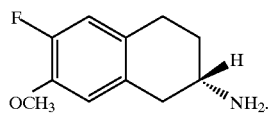

2. The salt of the compound of claim 1, having formula:

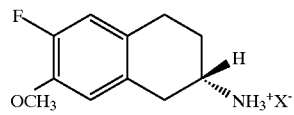

wherein X⁻ is the monovalent anion of a pharmacologically acceptable acid.

3. A salt according to claim 2, wherein the pharmacologically acceptable anion is selected from chloride, bromide, orotate, acid aspartate, acid citrate, acid phosphate, fumarate and acid fumarate, lactate, maleate and acid maleate, acid oxalate, acid solphate, glucose phosphate, tartrate and acid tartrate.

4. A process for preparing S(−)-2-amino-6-fluoro-7-methoxytetraline as free base or as a pharmacologically acceptable salt according to the reaction scheme:

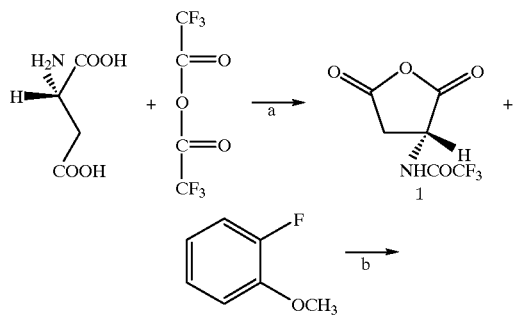

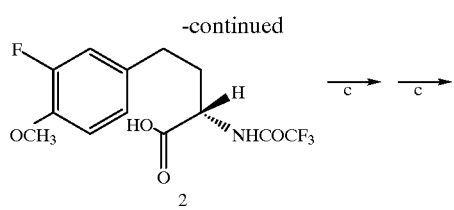

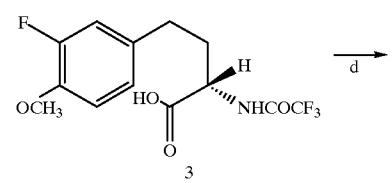

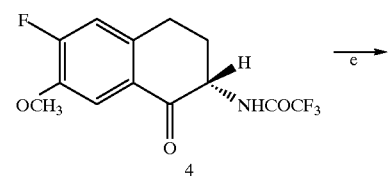

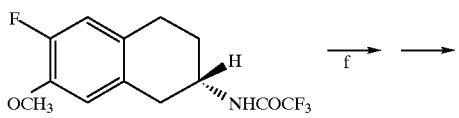

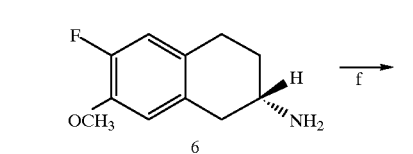

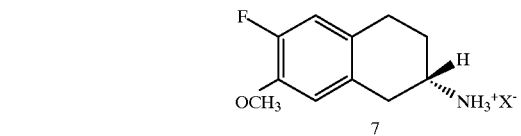

wherein X⁻ is the monovalent anion of a pharmacologically acceptable acid, comprising the steps consisting of:

(a) preparing an anhydride 1 by suspending L(+)-aspartic acid in CF₃COOH, adding cold trifluoroacetic anhydride and then heating the resulting mixture to the reflux temperature until the reaction is completed;

(b) condensing the anhydride 1 with an excess of 2-fluoroanisole (1.5–3 moles) in the presence of AlCl₃ at 40–60° C., for 40–50 hours, thus obtaining the acid 2;

(c) reducing the acid 2 by dissolving it with CF₃COOH, cooling the solution thus obtained at 0–8° C., adding an excess amount of triethylsilane and heating the mixture to the reflux temperature until the reaction is completed, thus obtaining the compound 3;

(d) preparing the tretralone 4 from the compound 3 by condensation via Friedel-Crafs reaction, with PCl₅ and AlCl₃ in an inert anhydrous organic solvent;

(e) reducing the tetralone 4 by suspending it in boroetherate trifluoride and adding an excess amount of triethylsilane at 0–8° C. and letting the reaction to proceed at room temperature until the reaction is completed, adding an aqueous alkaline solution, extracting the aqueous phase with a solvent, bringing to dryness and purifying by crystallization, thus obtaining the compound 5;

(f) hydrolyzing the compound 5 with an aqueous alkaline solution, obtaining S(−)-2-amino-6-fluoro-7-metoxytetraline 6; and (g) optionally solubilizing the compound 6 in an organic solvent, acidifying with the desired H⁺X⁻ acid and bringing to dryness, thus obtaining the salt 7.

5. An orally or parenterally administrable pharmaceutical composition for preventing and treating septic shock comprising a compound of claim 1, as active ingredient and a pharmacologically acceptable excipient.

6. A method of treating septic shock comprising administering to a patient in need of same an effective amount of S(−)-2-amino-6-fluoro-7-methoxytetraline having formula:

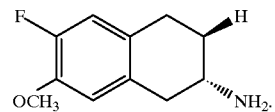

7. A method of treating septic shock comprising administering to a patient in need of same an effective amount of the salt of the compound of claim 1, having formula:

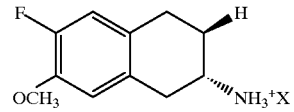

wherein X is a monovalent anion of a pharmacologically acceptable acid.

8. The method of claim 7 wherein the pharmacologically acceptable anion is selected from chloride, bromide, orotate, acid aspartate, acid citrate, acid phosphate, fiumarate, acid fuimarate, lactate, maleate, acid maleate, acid oxalate, acid sulphate, glucose phosphate, tartrate and acid tartrate.

* * * * *